(12) United States Patent
Arndt et al.

(10) Patent No.: US 6,645,918 B1
(45) Date of Patent: Nov. 11, 2003

(54) N-([1,2,4]TRIAZOLOAZINYL) THIOPHENESULFONAMIDE COMPOUNDS AND THEIR USE AS HERBICIDES

(75) Inventors: Kim Eric Arndt, Carmel, IN (US); Timothy Calvin Johnson, Indianapolis, IN (US); David George Ouse, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/326,730

(22) Filed: Dec. 19, 2002

Related U.S. Application Data

(62) Division of application No. 10/000,873, filed on Nov. 2, 2001, now Pat. No. 6,518,222.
(60) Provisional application No. 60/246,115, filed on Nov. 3, 2000.

(51) Int. Cl.[7] .................. A01N 43/54; C07D 487/04

(52) U.S. Cl. ...................... 504/241; 544/263

(58) Field of Search ............... 544/263; 504/241

(56) References Cited

U.S. PATENT DOCUMENTS

| | | | |
|---|---|---|---|
| 4,028,373 A | 6/1977 | Hromatka et al. | 260/301 |
| 4,638,075 A | 1/1987 | Kleschick et al. | 558/5 |
| 4,650,892 A | 3/1987 | Kleschick et al. | 558/5 |
| 4,685,958 A | 8/1987 | Pearson et al. | 71/93 |
| 4,822,404 A | 4/1989 | Kleschick | 71/92 |
| 5,163,995 A | 11/1992 | Van Heertum et al. | 71/92 |
| 5,484,760 A | 1/1996 | Bussler et al. | 504/103 |
| 5,571,775 A | 11/1996 | Van Heertum et al. | 504/246 |
| 5,571,821 A | 11/1996 | Chan et al. | 514/312 |
| 5,858,924 A | 1/1999 | Johnson et al. | 504/241 |
| 5,880,066 A | 3/1999 | Wells et al. | 504/103 |
| 5,965,490 A | 10/1999 | Johnson et al. | 504/246 |
| 6,005,108 A | 12/1999 | Johnson et al. | 544/263 |

FOREIGN PATENT DOCUMENTS

| | | |
|---|---|---|
| DE | 3539386 A1 | 11/1985 |
| DE | 4106100 A1 | 2/1991 |
| WO | WO98/13367 | 4/1998 |

OTHER PUBLICATIONS

Database Crossfire Beilstein Online!; Beilstein Institut zur Forderung der Chemischen Wissenschaften, Frankfurt am Main, DE; Datbase accession No. 120654, 130711, 130712, 130710 (BRN); XP002193053; abstract & Justus Liebigs Ann. Chem., vol. 512, 1934, p. 136.

Database Crossfire Beilstein Online!; Beilstein Institut zur Forderung der Chemischen Wissenschaften, Frankfurt am Main, DE; Datbase accession No. 136792 (BRN); XP002193069; abstract & J. Chem. Soc., 1948, p. 769.

Database Crossfire Beilstein Online!; Beilstein Institut zur Forderung der Chemischen Wissenschaften, Frankfurt am Main, DE; Datbase accession No. 188148 (BRN); XP002193067; abstract & J. Am. Pharm. Assoc., vol. 41, 1952, p. 273.

Database Crossfire Beilstein Online!; Beilstein Institut zur Forderung der Chemischen Wissenschaften, Frankfurt am Main, DE; Datbase accession No. 123536 (BRN); XP002193060; abstract & J. Chem. Soc., 1956, p. 4114.

Database Crossfire Beilstein Online!; Beilstein Institut zur Forderung der Chemischen Wissenschaften, Frankfurt am Main, DE; Datbase accession No. 175032 (BRN); XP002193068; abstract & Justus Liebigs Ann. Chem., vol. 634, 1960, p. 185.

Database Crossfire Beilstein Online!; Beilstein Institut zur Forderung der Chemischen Wissenschaften, Frankfurt am Main, DE; Datbase accession No. 1239349, 1239762 (BRN); XP002193058; abstract & Bull. Chem. Soc. Jpn., vol. 34, 1961, p. 1599.

Database Crossfire Beilstein Online!; Beilstein Institut zur Forderung der Chemischen Wissenschaften, Frankfurt am Main, DE; Datbase accession No. 123911 (BRN); XP002193070; abstract & Nippon Kagaku Zasshi, vol. 83, 1962, p. 496.

Database Crossfire Beilstein Online!; Beilstein Institut zur Forderung der Chemischen Wissenschaften, Frankfurt am Main, DE; Datbase accession No. 1241435 (BRN); XP002193066; abstract & Soc. Sci. Lodz. Acta Chim., vol. 14, 1969, p. 95.

Database Crossfire Beilstein Online!; Beilstein Institut zur Forderung der Chemischen Wissenschaften, Frankfurt am Main, DE; Datbase accession No. 4435344 (BRN); XP002193056; abstract & J. Org. Chem., vol 45, No. 4, 1980, pp. 617–620.

Database Crossfire Beilstein Online!; Beilstein Institut zur Forderung der Chemischen Wissenschaften, Frankfurt am Main, DE; Datbase accession No. 2723948, 6397023 (BRN); XP002193065; abstract & Phosphorus Sulfur, vol 10, 1981, pp. 111–120.

Database Crossfire Beilstein Online!; Beilstein Institut zur Forderung der Chemischen Wissenschaften, Frankfurt am Main, DE; Datbase accession No. 5014060, 5013168 (BRN); XP002193064; abstract & J. Med. Chem., vol. 24, No. 8, 1981, pp. 959–964.

(List continued on next page.)

Primary Examiner—John M. Ford
(74) Attorney, Agent, or Firm—Craig E. Mixan

(57) ABSTRACT

N-(Triazolo[1,5-a]pyrimidinyl)thiophenesulfonamide compounds were prepared from appropriately substituted 2-amino[1,2,4]triazolo[1,5-a]pyrimidine compounds and appropriately substituted thiophenesulfonyl chloride compounds. The compounds were found to be useful as herbicides.

15 Claims, No Drawings

OTHER PUBLICATIONS

Database Crossfire Beilstein Online!; Beilstein Institut zur Forderung der Chemischen Wissenschaften, Frankfurt am Main, DE; Datbase accession No. 6391697 (BRN); XP002193062; abstract & J. Chem. Soc. Perkin Trans. 2, 1986, pp. 1179–1182.

Database Crossfire Beilstein Online!; Beilstein Institut zur Forderung der Chemischen Wissenschaften, Frankfurt am Main, DE; Datbase accession No. 5814781 (BRN); XP002193057; abstract & J. Med. Chem., vol. 30, No. 4, 1987, pp. 678–682.

Database Crossfire Beilstein Online!; Beilstein Institut zur Forderung der Chemischen Wissenschaften, Frankfurt am Main, DE; Datbase accession No. 5864899, 1283273 (BRN); XP002193063; abstract & J. Med. Chem., vol. 35, No. 16, 1992, pp. 3012–3016.

Database Crossfire Beilstein Online!; Beilstein Institut zur Fordenrung der Chemischen Wissenschaften, Frankfurt am Main, DE; Datbase accession No. 7992992 (BRN); XP002193061; abstract & Bioorg. Med. Chem., vol. 6, No. 6, 1998, pp. 673–686.

N-([1,2,4]TRIAZOLOAZINYL) THIOPHENESULFONAMIDE COMPOUNDS AND THEIR USE AS HERBICIDES

CROSS-REFERENCE TO RELATED APPLICATIONS

This application is a divisional of U.S. application Ser. No. 10/000,873 filed Nov. 2, 2001, now U.S. Pat. No. 6,518,222, filed Feb. 11, 2003, claiming the benefits of U.S. Provisional Application No. 60/246,115 filed Nov. 3, 2000.

BACKGROUND OF THE INVENTION

The present invention relates to substituted thiophenesulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

Many substituted benzenesulfonamide compounds are known and certain of them are known to possess herbicidal activity. For example, certain N-([1,2,4]triazolo[1,5-a]pyrimidin-2-yl)benzenesulfonamide compounds and their herbicidal utility were disclosed in U.S. Pat. No. 4,638,075 and certain N-([1,2,4]triazolo[1,3,5]triazin-2-yl)benzenesulfonamide compounds were disclosed in U.S. Pat. No. 4,685,958. In addition, certain N-([1,2,4]triazolo[1,5-c]pyrimidin-2-yl)benzenesulfonamide, N-([1,2,4]triazolo[1,5-c]pyrimidin-2-yl)pyridinesulfonamide, N-([1,2,4]triazolo[1,5-a]pyridin-2-yl)benzenesulfonamide, and N-([1,2,4]triazolo[1,5-a]pyridin-2-yl)pyridinesulfonamide compounds were disclosed in U.S. Pat. No. 5,858,924. Certain N-phenyl arylsulfonamide compounds are also known and are known to possess herbicidal activity. For example, certain N-(substituted phenyl)[1,2,4]triazolo[1,5-c]pyrimidin-2-sulfonamide compounds were disclosed in U.S. Pat. No. 5,163,995 and certain N-(substituted phenyl)[1,2,4]triazolo[1,5-a]pyridin-2-sulfonamide compounds were disclosed in U.S. Pat. No. 5,571,775.

SUMMARY OF THE INVENTION

It has now been found that a class of novel N-(triazoloazinyl)thiophenesulfonamide compounds comprising N-([1,2,4]triazolo[1,5-c]pyrimidin-2-yl)thiophenesulfonamide, N-([1,2,4]triazolo[1,5-a]pyrimidin-2-yl)thiophenesulfonamide, and N-([1,2,4]triazolo[1,5-a]pyridin-2-yl)thiophenesulfonamide compounds are potent herbicides for the control of unwanted vegetation by either preemergence or post-emergence application. The invention includes N-(triazoloazinyl)thiophenesulfonamide compounds of Formula I:

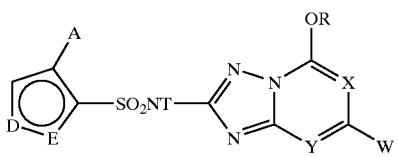

(I)

wherein
X represents CH or
Y represents CZ or N with the proviso that X and Y are not both N;

W represents H or OR with the proviso that when Y is CZ, then W is H;
Z represents R, OR or halo;
D and E represent S or CB with the proviso that one of D or E is S;
A and B independently represent H, halo, $CF_3$, R, OR' or $CO_2R''$;
T represents H, $SO_2R''$, $C(O)R''$, $C(O)OR''$, $C(O)NR''_2$, or $CH_2CH_2C(O)OR''$;
R represents $CH_3$ or $CH_2CH_3$;
R' represents $C_1$–$C_4$ alkyl, $C_3$–$C_4$ alkenyl, or $C_3$–$C_4$ alkynyl each optionally possessing up to two chloro, bromo or $O(C_1$–$C_4)$alkyl substituents or up to the maximum possible number of fluoro substituents;
R" represents H or $C_1$–$C_4$ alkyl;
and, when T represents H, the agriculturally acceptable salts thereof.

Compounds wherein A represents OR' or B represents $CO_2R''$ when D represents S and T represents H are among the preferred compounds of the invention.

The invention further includes compositions containing herbicidal amounts of compounds of Formula I in combination with one or more agriculturally acceptable adjuvants or carriers and the use of the compounds of Formula I as herbicides. The use of suitable compounds of the invention to achieve total vegetation control is generally preferred. Both grassy and broadleaf weeds can be controlled. Post-emergence application of the compounds to undesirable vegetation is generally preferred.

DETAILED DESCRIPTION OF THE INVENTION

The N-(triazoloazinyl)thiophenesulfonamide compounds of the invention can generally be described as substituted N-([1,2,4]triazolo[1,5-c]pyrimidin-2-yl)thiophenesulfonamide, N-([1,2,4]triazolo[1,5-a]pyrimidin-2-yl)thiophenesulfonamide, and N-([1,2,4]triazolo[1,5-a]pyridin-2-yl)thiophenesulfonamide compounds. They can be characterized as substituted thiophenesulfonamide compounds possessing, on the amide nitrogen atom, a substituted [1,2,4]triazolo[1,5-c]pyrimidin-2-yl, a substituted [1,2,4]triazolo[1,5-a]pyrimidin-2-yl or a substituted [1,2,4]triazolo[1,5-a]pyridin-2-yl moiety.

The herbicidal compounds of the invention are N-(triazoloazinyl)thiophenesulfonamide compounds of generic Formula I:

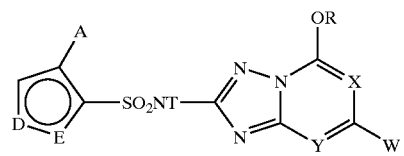

(I)

Such compounds in which X represents N contain a substituted N-([1,2,4]triazolo[1,5-c]pyrimidin-2-yl) moiety, those in which Y represents N contain a substituted N-([1,2,4]triazolo[1,5-a]pyrimidin-2-yl) moiety and those in which X represents C—H and Y represents C—Z contain a substituted N-([1,2,4]triazolo[1,5-a]pyridin-2-yl) moiety. Compounds in which E represents S are 2-thiophenesulfonamide compounds and compounds in which D represents S are 3-thiophenesulfonamide compounds. The compounds are further characterized by possessing a methoxy or an ethoxy substituent adjacent to the bridgehead nitrogen in the 6-membered ring portion of the triazoloazine ring and by possessing at least one substituent (A) adjacent to the sulfonamide on the thiophene ring.

The compounds of the invention include compounds of Formula I wherein X is N or CH.

Compounds in which X is N are often preferred. However, compounds in which X is CH are sometimes preferred.

The compounds of the invention include compounds of Formula I wherein Y is N, provided that X is not also N, or CZ in which Z is methyl, ethyl, methoxy, ethoxy or halo. Compounds in which Y is CZ are often preferred. However, compounds in which Y is N are sometimes preferred. Compounds in which Z is methoxy are often preferred.

Compounds of the invention include compounds of Formula I wherein D and E represent S or CB, provided that one and only one of D or E is S. The thiophene-3-sulfonamides in which D represents S are usually preferred.

Compounds of the invention include compounds of Formula I wherein A and B independently represent H, halo, $CF_3$, R, OR' or $CO_2R''$. A is preferably OR' or $CO_2R''$, and most preferably OR'.

Compounds of the invention include compounds of Formula I wherein W represents H or OR provided that when Y is CZ, W is H. When Y is N, W is preferably methoxy.

For compounds of the present invention, R can be $CH_3$ or $CH_2CH_3$. For OR, R is preferably $CH_3$.

For compounds of the present invention, R' can be $C_1$–$C_4$ alkyl, $C_3$–$C_4$ alkenyl, or $C_3$–$C_4$ alkynyl each optionally possessing up to two chloro, bromo or $O(C_1$–$C_4)$alkyl substituents or up to the maximum possible number of fluoro substituents. For OR', R' is preferably $C_1$–$C_4$ alkyl optionally possessing up to two chloro, bromo or $O(C_1$–$C_4)$alkyl substituents or up to the maximum possible number of fluoro substituents.

The compounds of Formula I include those wherein T represents hydrogen, an alkylsulfonyl group ($SO_2R''$), an acyl group (C(O)R''), an alkoxycarbonyl group (C(O)OR''), an aminocarbonyl group (C(O)NR''$_2$), or a 2-(alkoxycarbonyl) ethyl group ($CH_2CH_2C(O)OR''$). Such compounds wherein T represents hydrogen are preferred. The invention further includes the agriculturally acceptable salts of compounds of the Formula I wherein T represents hydrogen.

For compounds of the present invention, R'' can be H or $C_1$–$C_4$ alkyl. R'' is preferably $CH_3$ or $CH_2CH_3$.

Compounds of Formula I which possess each possible combination of preferred, more preferred, most preferred, desirable, and special interest substituents are, further, considered to be important embodiments of the invention.

The terms alkyl, alkenyl, and alkynyl (including when modified as in haloalkyl and alkoxy) as used herein include straight chain, branched chain, and cyclic groups. Thus, typical alkyl groups are methyl, ethyl, 1-methylethyl, propyl, 1,1-dimethylethyl and cyclopropyl. Methyl and ethyl are often preferred. Alkyl groups are sometimes referred to herein as normal (n), iso (i), secondary (s) or tertiary (t). Typical alkyl with up to the maximum possible number of fluoro substituents include trifluoromethyl, monofluoromethyl, 2,2,2-trifluoroethyl, 2,3-difluoropropyl, and the like; trifluoromethyl is often preferred. The term halogen includes fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$$R^2R^3R^4NH^+$$

wherein $R^2$, $R^3$, and $R^4$ each, independently represents hydrogen or $(C_1$–$C_{12})$alkyl, $(C_3$–$C_{12})$cycloalkyl, or $(C_3$–$C_{12})$alkenyl, each of which is optionally substituted by one or more hydroxy, $(C_1$–$C_8)$alkoxy, $(C_1$–$C_8)$alkylthio or phenyl groups; provided that $R^2$, $R^3$, and $R^4$ are sterically compatible. Additionally, any two of $R^2$, $R^3$ and $R^4$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide or magnesium hydroxide, or an amine, such as ammonia, trimethylamine, hydroxyethylamine, bisallylamine, 2-butoxyethylamine, morpholine, cyclododecylamine or benzylamine.

The compounds of Table 1 and 2 are examples of the compounds of the invention. Some of the specifically preferred compounds of Formula I, which vary depending on the weed species to be controlled, the crop present (if any), and other factors, include the following compounds of Table 1 and 2: N-(5,8-dimethoxy[1,2,4]triazolo[1,5-c]pyrimidin-2-yl)-4-methoxythiophene-3-sulfonamide and N-(5,8-dimethoxy[1,2,4]triazolo[1,5-c]pyrimidin-2-yl)-2-carboxymethylthiophene-3-sulfonamide.

TABLE 1

SULFONAMIDE COMPOUNDS

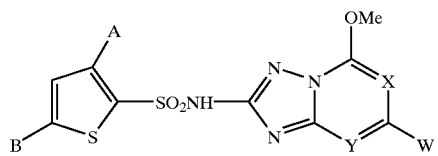

| Cpd. No. | A | B | X | Y | W | Form | Melting Point, °C. | Elem. Anal. Calc./Found | | |
|---|---|---|---|---|---|---|---|---|---|---|
| | | | | | | | | % C | % H | % N |
| 1 | $OCH_3$ | H | N | C—$OCH_3$ | H | Tan Powder | 227–228 | 38.81 38.32 | 3.53 3.49 | 18.86 18.91 |
| 2 | $OCH_3$ | H | N | C—Cl | H | Pink Powder | 226–227 | 35.16 35.50 | 2.68 2.83 | 18.64 18.30 |

TABLE 1-continued

SULFONAMIDE COMPOUNDS

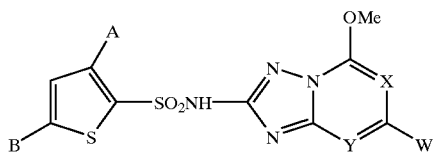

| Cpd. No. | A | B | X | Y | W | Form | Melting Point, °C. | Elem. Anal. Calc./Found %C | %H | %N |
|---|---|---|---|---|---|---|---|---|---|---|
| 3 | OCH₃ | Cl | N | C—OCH₃ | H | White Powder | 221–222 | 35.52 / 35.65 | 2.98 / 2.94 | 17.26 / 16.99 |
| 4 | OCH₃ | Cl | CH | N | OCH₃ | White Powder | 218–219 | 35.52 / 35.44 | 2.98 / 2.89 | 17.26 / 16.91 |
| 5 | OCH₃ | CF₃ | CH | N | OCH₃ | Tan Powder | 218–219 | 35.54 / 35.77 | 2.75 / 2.76 | 15.94 / 15.51 |

TABLE 2

SULFONAMIDE COMPOUNDS

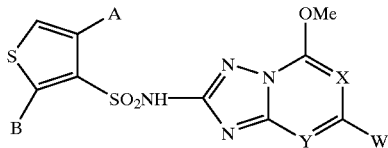

| Cpd. No. | A | B | X | Y | W | Form | Melting Point, °C. | Elem. Anal. Calc./Found %C | %H | %N |
|---|---|---|---|---|---|---|---|---|---|---|
| 6 | H | CO₂CH₃ | N | C—OCH₃ | H | Tan Powder | 277–279 | 39.09 / 38.72 | 3.38 / 3.13 | 17.53 / 17.09 |
| 7 | OCH₃ | H | N | C—OCH₃ | H | White Powder | 236–237 | 38.81 / 39.05 | 3.53 / 3.54 | 18.86 / 18.55 |
| 8 | H | OCH₃ | N | C—OCH₃ | H | Gray Powder | 220–221 | 38.81 / 38.83 | 3.53 / 3.45 | 18.86 / 18.66 |
| 9 | H | OCH₃ | N | C—CH₃ | H | White Powder | 220–221 | 40.56 / 40.59 | 3.69 / 3.60 | 19.71 / 19.65 |
| 10 | OCH₃ | CF₃ | N | C—OCH₃ | H | Tan Powder | 231–232 | 35.54 / 35.28 | 2.75 / 2.71 | 15.94 / 15.67 |
| 11 | OC₂H₅ | H | CH | C—OCH₃ | H | White Powder | 246–247 | 43.74 / 43.52 | 4.20 / 4.19 | 14.57 / 14.32 |
| 12 | OC₂H₅ | H | CH | N | OCH₃ | Tan Powder | 194–195 | 40.51 / 40.16 | 3.92 / 3.87 | 18.17 / 17.91 |
| 13 | OC₂H₅ | H | N | C—OCH₃ | H | White Powder | 223–224 | 40.51 / 40.18 | 3.92 / 3.89 | 18.17 / 17.89 |
| 14 | OCH₃ | H | N | C—Cl | H | White Powder | 208–209 | 35.16 / 34.95 | 2.68 / 2.68 | 18.64 / 18.61 |
| 15 | OCH₃ | H | CH | N | OCH₃ | White Powder | 218–219 | 38.81 / 38.63 | 3.53 / 3.35 | 18.86 / 18.60 |
| 16 | OCH₃ | H | CH | C—OCH₃ | H | White Powder | 245–246 | 42.16 / 42.42 | 3.81 / 3.80 | 15.13 / 15.06 |
| 17 | OCH₃ | H | N | C—CH₃ | H | White Powder | 230–231 | 40.56 / 40.36 | 3.69 / 3.61 | 19.71 / 19.68 |
| 18 | OCH₃ | Cl | N | C—OCH₃ | H | Tan Powder | 222–223 | 35.52 / 35.53 | 2.98 / 2.99 | 17.26 / 17.10 |
| 19 | OCH₃ | Cl | CH | N | OCH₃ | White Powder | 205–206 | 35.52 / 35.16 | 2.98 / 2.90 | 17.26 / 17.23 |
| 20 | OCH₃ | Cl | N | C—Cl | H | White Powder | 208–210 | 32.21 / 32.14 | 2.21 / 2.21 | 17.07 / 16.97 |
| 21 | OCH₃ | Cl | N | C—CH₃ | H | White Powder | 212–214 | 36.97 / 36.78 | 3.10 / 3.04 | 17.97 / 17.70 |
| 22 | OCH₃ | CH₃ | N | C—Cl | H | White Powder | 220–221 | 36.97 / 37.14 | 3.10 / 3.14 | 17.97 / 17.82 |
| 23 | OCH₃ | CH₃ | N | C—OCH₃ | H | White Powder | 219–220 | 40.51 / 40.67 | 3.92 / 3.98 | 18.17 / 17.90 |

TABLE 2-continued

SULFONAMIDE COMPOUNDS

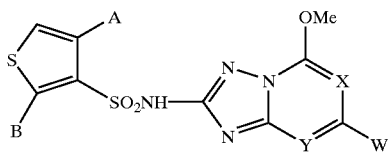

| Cpd. No. | A | B | X | Y | W | Form | Melting Point, °C. | Elem. Anal. Calc./Found % C | % H | % N |
|---|---|---|---|---|---|---|---|---|---|---|
| 24 | OCH₃ | CH₃ | CH | N | OCH₃ | White Powder | 209–210 | 40.51 / 39.98 | 3.92 / 3.83 | 18.17 / 18.27 |
| 25 | OCH₃ | CF₃ | CH | N | OCH₃ | Tan Powder | 219–221 | 35.54 / 35.66 | 2.75 / 2.78 | 15.94 / 15.31 |

The compounds of Formula I wherein T represents hydrogen can be prepared by the reaction of a substituted 2-amino [1,2,4]triazoloazine compound of Formula II:

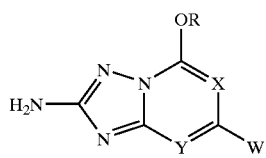

(II)

with a thiophenesulfonyl chloride compound of Formula III:

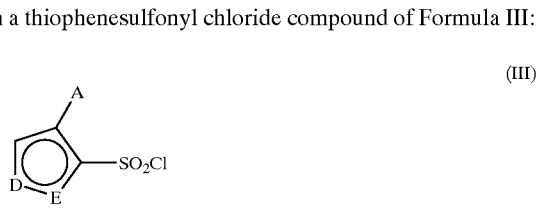

(III)

wherein A, D, E, R, W, X and Y are as defined for compounds of Formula I. The reaction can be carried out by combining approximately equal molar amounts of the two compounds in a polar, aprotic solvent, such as acetonitrile, and adding pyridine and a catalytic amount (5 to 25 molar percent of the sulfonyl chloride compound) of dimethyl sulfoxide at room temperature. Additional sulfonyl chloride compound, pyridine, and dimethyl sulfoxide are added, if necessary, to complete the reaction. The reactions take from a few hours to several days to go to completion. Means to exclude moisture, such as a dry nitrogen blanket, are employed. The compounds of Formula I obtained, which are solids with low solubility in many common organic solvents and in water, can be recovered using conventional means.

N-(triazoloazinyl)thiophenesulfonamide compounds of Formula I wherein T represents other than hydrogen can be prepared from the corresponding compounds of Formula I wherein T represents hydrogen by acylation under reaction conditions known in the art for related sulfonamide acylation reactions. Suitable acylating agents include alkanoyl chloride compounds, such as propionyl chloride or trifluoroacetyl chloride; chloroformate ester compounds, such as 2-methoxyethyl chloroformate; carbamoyl chloride compounds, such as N',N'-diallylcarbamoyl chloride, and alkyl isocyanate compounds, such as 2-chloroethyl isocyanate.

Compounds of Formula I having alkoxy substituents in the triazoloazine ring can be prepared from the corresponding halo compounds of Formula I by treatment with an appropriate alkoxide using the general methods for such replacements known in the art. Halo substituents in some positions are generally more easily replaced than are halo substituents in other positions depending on the triazoloazine ring system and can be selectively replaced.

Many 2-amino[1,2,4]triazolo[1,5-a]pyridine compounds of Formula II (X represents C—H and Y represents C—Z) can be prepared by the reaction of appropriately substituted N-(2-pyridinyl)-N'-carboethoxythiourea compounds of the formula:

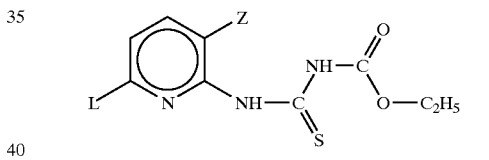

wherein Z is as defined for compounds of Formula I and L is OR or halo, with hydroxylamine. The reaction is typically carried out in a solvent such as ethanol and requires heating for a few hours. The hydroxylamine is typically generated by neutralization of the hydrochloride with a hindered tertiary amine, such as diisopropylethylamine, or an alkali metal alkoxide, such as sodium ethoxide. The desired compounds of Formula II can be recovered by conventional means, such as by removal of the volatile components of the reaction mixture by evaporation, and can be purified by conventional means, such as by extraction with water and/or other solvents in which they are sparingly soluble. The N-(2-pyridinyl)-N'-carboethoxythiourea compound starting materials for this method can be obtained by treatment of appropriately substituted 2-aminopyridine compounds with ethoxycarbonyl isothiocyanate. The reaction is generally carried out in an inert organic solvent at ambient temperatures. The overall method is further described in U.S. Pat. No. 5,571,775.

The substituted 2-aminopyridine compound starting materials for the method described above are known in the art or can be prepared by the methods disclosed herein or by general methods known in the art.

Compounds of Formula II wherein X represents C—H can also be prepared from appropriately substituted 2-cyanoaminopyridine compounds by the method disclosed by B. Vercek et al. in *Monatshefte fur Chemie*, 114, 789–798 (1983). Additional methods of preparation of such compounds were disclosed by K. T. Potts et al. in *Journal of Organic Chemistry*, 31, 265–273 (1966).

Compounds of Formula II wherein X represents N, i.e., 2-amino[1,2,4]triazolo[1,5-c]pyrimidine compounds, can be prepared from 4-hydrazinopyrimidine compounds of the formula:

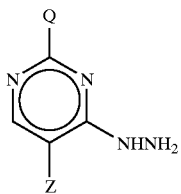

wherein Q represents methylthio or chloro and Z is as defined for compounds of Formula I. The hydrazinopyrimidine compound is first treated with cyanogen bromide to produce the hydrobromide of a 3-amino-8-substituted-5-substituted[1,2,4]triazolo[4,3-c]pyrimidine compound of the formula:

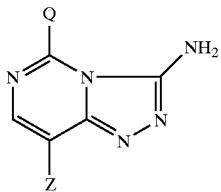

wherein Q represents methylthio or chloro and Z is as defined for compounds of Formula I. The reaction is generally carried out in an organic solvent, such as isopropyl alcohol, at ambient temperature. The products can be recovered by conventional means, such as by adding a non-polar solvent, for example diethyl ether, and collecting the solid that forms by filtration. The above intermediates wherein Q represents methylthio can then be converted into the desired compounds of Formula II wherein Q represents an alkoxy group by treatment with an alkali metal alcoholate, such as sodium methylate or potassium ethylate, and ethyl acrylate in the corresponding alcohol as a solvent. The compound rearranges and the methylthio moiety is replaced by the alkoxy moiety derived from the alcohol of the medium. The reaction is generally carried out at temperatures below 25° C. The desired compounds of Formula II can be recovered by neutralizing with acetic acid and collecting the solids that form by filtration or other conventional means. Compounds of Formula II wherein X represents N and Q represents chloro can be obtained from the corresponding [4,3-c] intermediate wherein Q represents chloro by isomerization with a trialkylamine base. The 4-hydrazinopyrimidine compound starting materials for these methods can be prepared from the corresponding 4-chloropyrimidine compounds, which are well-known in the art, by reaction with hydrazine.

Other methods of preparation of compounds of Formula II wherein X represents N are disclosed by G. W. Miller, et al., *J. Chemical Society*, 1965, page 3357 and 1963, page 5642.

Compounds of Formula II wherein Y represents N, e.g., 2-amino[1,2,4]triazolo[1,5-a]pyrimidine compounds, can be prepared by the reaction of N-(4,6-dialkoxypyrimidin-2-yl)-N'-carboethoxythiourea of the formula:

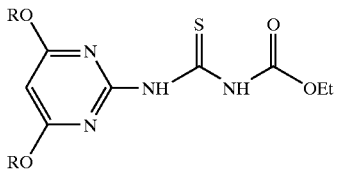

wherein R is as defined for Formula I with hydroxylamine. The reaction is typically carried out in a solvent such as ethanol and requires heating for a few hours. The hydroxylamine is typically generated by neutralization of the hydrochloride with a hindered tertiary amine, such as diisopropylethylamine, or an alkali metal alkoxide, such as sodium ethoxide. The desired compound of Formula II can be recovered by conventional means, such as by removal of the volatile components of the reaction mixture by evaporation, and can be purified by conventional means, such as by extraction with water and/or other solvents in which they are sparingly soluble. The N-(4,6-dialkoxypyrimidin-2-yl)-N'-carboethoxythiourea starting material for this method can be obtained by treatment of 2-amino-4,6-dialkoxypyrimidine with ethoxycarbonyl isothiocyanate. The reaction is generally carried out in an inert organic solvent at ambient temperatures. The overall method is further described in U.S. Pat. No. 5,571,775.

The 2-amino-4,6-dialkoxypyrimidine starting material for the method described above is known in the art.

The substituted thiophenesulfonyl chloride starting materials of Formula III can be prepared by the methods disclosed herein or by general or specific methods known in the art. Many such compounds can be prepared by lithiation of the corresponding thiophene compound with butyl lithium, reaction of the thienyl lithium compound obtained with $SO_2$, and then chlorination with N-chlorosuccinimide. In each of these reaction steps, conditions generally known for such processes were used. Thienyl lithium compounds can also be prepared by halogen-metal exchange reactions of halothiophenes with n-butyl lithium. Many propyl or benzylthiothiophenes can also be prepared by alkylation of the corresponding mercaptothiophene compound using standard methods or by reaction of the thienyl lithium compounds with the appropriate disulfide. Subsequent chloroxidation with, for example, chlorine in the presence of water provides the desired sulfonyl chlorides.

Compounds of Formula III include substituted thiophene-2-sulfonyl chloride compounds of the formula:

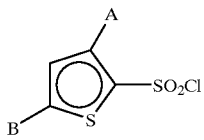

and substituted thiophene-3-sulfonyl chloride compounds of the formula:

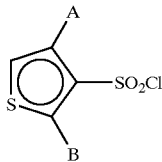

wherein A and B independently represent H, halo, $CF_3$, R, OR' or $CO_2R''$. The substituted thiophene-3-sulfonyl chlorides are preferred, particularly those in which A or B are OR' or $CO_2R''$.

While it is possible to utilize the N-(triazoloazinyl) thiophenesulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions can also contain other compatible components, for example, other herbicides, herbicide safeners, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence (including pre-plant) and postemergence herbicides. Postemergence applications are generally preferred. The compounds are effective in the control of both broadleaf and grassy weeds. While each of the N-(triazoloazinyl) thiophenesulfonamide compounds encompassed by Formula I is within the scope of the invention, the degree of herbicidal activity, crop selectivity, and spectrum of weed control obtained varies depending upon the substituents and other features present. The compounds can be employed at higher, non-selective rates of application to control essentially all of the vegetation in an area. In some cases, the compounds can also be employed at lower, selective rates of application for the control of undesirable vegetation in grass crops or in broadleaf crops. In some instances, the selectivity can often be improved by the use of safeners.

The term herbicide is used herein to mean an active ingredient that controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature plants to achieve the maximum control of weeds.

Application rates of about 0.001 to about 1 Kg/Ha are generally employed in postemergence operations; for preemergence applications, rates of about 0.01 to about 2 kg/ha are generally employed. The higher rates designated generally give non-selective control of a broad variety of undesirable vegetation. The lower rates typically give selective control and, by judicious election of compounds, timing, and rates of application, can be employed in the locus of crops.

The compounds of the present invention (Formula I) are often applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed beneficially in combination with the compounds of the present invention include substituted triazolopyrimidinesulfonamide compounds, such as diclosulam, cloransulam-methyl and flumetsulam. Other herbicides such as acifluorfen, bentazon, chlorimuron, clomazone, lactofen, carfentrazone-methyl, fumiclorac, fluometuron, fomesafen, imazaquin, imazethapyr, linuron, metribuzin, fluazifop, haloxyfop, glyphosate, glufosinate, 2,4-D, acetochlor, metolachlor, sethoxydim, nicosulfuron, clopyralid, fluroxypyr, metsulfuron-methyl, amidosulfuron, tribenuron, and others can also be employed. It is generally preferred to use the compounds in conjunction with other herbicides that have a similar crop selectivity. It is further usually preferred to apply the herbicides at the same time, either as a combination formulation or as a tank mix.

The compounds of the present invention can generally be employed in combination with a wide variety of known herbicide safeners, such as cloquintocet, mefenpyr, furilazole, dichlormid, benoxacor, flurazole, fluxofenim, daimuron, dimepiperate, thiobencarb, and fenclorim, to enhance their selectivity. Herbicide safeners that act by modifying the metabolism of herbicides in plants by enhancing the activity of cytochrome P-450 oxidases are usually especially effective. This is often a preferred embodiment of the invention. The compounds can additionally be employed to control undesirable vegetation in many crops that have been made tolerant to or resistant to herbicides by genetic manipulation or by mutation and selection. For example, crops that have been made tolerant or resistant to herbicides in general or to herbicides that inhibit the enzyme acetolactate synthase in sensitive plants can be treated.

EXAMPLES

The following Examples are presented to illustrate the various aspects of this invention and should not be construed as limitations to the claims.

1. Preparation of Methyl 4-Bromo-3-hydroxy-2-thiophenecarboxylate

To a solution of 31 g (0.2 mole) of methyl 3-hydroxy-2-thiophenecarboxylate in 400 milliliters (mL) of glacial acetic acid was added 31.3 g (0.2 mole) of $Br_2$ over 45 minutes (min). After 16 hours (hr), another 31.3 g of $Br_2$ was added over 6 hr and the reaction was stirred another 18 hr. The reaction mixture was poured into aqueous $NaHSO_3$ and extracted with ether. The organic phase was separated, washed with water (2×300 mL), dried over $MgSO_4$, filtered and concentrated to a viscous oil. This oil (47 g) was dissolved in 200 mL of methanol and after 48 hr at 15° C., 36 g (77%) of light pink crystals were collected by filtration. mp 79–80° C. $^1$H NMR (300 MHz, $CDCl_3$): δ 9.8 (br, 1H); 7.4 (s, 1H); 3.9 (s, 3H). Anal. Calc'd for $C_6H_5BrO_3S$: C, 30.04; H, 2.23; S, 13.52. Found: C, 30.04; H, 1.92; S, 14.01.

2. Preparation of Methyl 4-Bromo-3-methoxy-2-thiophenecarboxylate

To a solution of 36 g (0.15 mole) of methyl 4-bromo-3-hydroxy-2-thiophenecarboxylate in 300 mL of dimethyl sulfoxide (DMSO) was added 32 g (0.23 mole) of methyl iodide and then 32 g of powdered $K_2CO_3$. After 2 hr, the reaction mixture was poured into water and extracted with ether. The organic phase was washed with water (4×200 mL), dried over $MgSO_4$, filtered and concentrated to give 36 g of a colorless solid. $^1$H NMR (300 MHz, $CDCl_3$): δ 7.4 (s, 1H); 4.0 (s, 3H); 3.9 (s, 3H). Anal. Calc'd for $C_7H_7BrO_3S$: C, 33.48; H, 2.81; S, 12.77. Found: C, 33.18; H, 2.70; S, 12.49.

3. Preparation of 4-Bromo-2-carboxy-3-methoxythiophene

A solution of 37.5 g (0.15 mole) of methyl 4-bromo-3-methoxy-2-thiophenecarboxylate and 12 g of KOH (0.18 mole) in a mixture of 250 mL of methanol and 100 mL of water was refluxed for 2 hr. The reaction mixture was cooled and most of the methanol was removed in vacuo. The solution was partitioned with ether and dilute aqueous HCl. The organic phase was separated dried over $MgSO_4$, filtered and concentrated and dried under a vacuum to give 34 g (94%) of a colorless solid. mp 191–192° C. $^1$H NMR (300 MHz, $CDCl_3$): δ 7.5 (s, 1H); 4.1 (s, 3H). Anal. Calc'd for $C_6H_5BrO_3S$: C, 30.04; H, 2.23; S, 13.52. Found: C, 29.89; H, 2.06; S, 13.14.

4. Preparation of 4-Bromo-2-carboxy-5-chloro-3-methoxythiophene

A solution of lithium diisopropylamine (LDA) was prepared at −10° C. by the addition of 88.6 mL (0.22 mole) of 2.5 M n-butyllithium to a solution of 22.4 g (0.22 mole) of diisopropylamine in 150 mL of dry tetrahydrofuran (THF). This was then slowly added to a colorless solution of 15 g (63 mmole) of 4-bromo-2-carboxy-3-methoxythiophene in 200 mL of dry THF at −78° C. to give a deep red solution. After 1 hr, 60 g (0.25 mole) of $C_2Cl_6$ was added and the reaction mixture allowed to warm slowly to room temperature. The reaction mixture was partitioned with ether and dilute aqueous HCl. The organic phase was then extracted several times with 5% aqueous NaOH. The aqueous extracts were combined, acidified with 20% aqueous HCl and extracted with fresh ether. The organic layer was dried over $MgSO_4$, filtered and concentrated to give 16.1 g (94%) of a tan solid. mp 191–192° C. $^1$H NMR (300 MHz, $CDCl_3$): δ 4.1 (s, 3H). Anal. Calc'd for $C_6H_4BrClO_3S$: C, 26.54; H, 1.48; S, 11.81. Found: C, 27.02; H, 1.55; S, 11.42.

5. Preparation of 4-Bromo-2-carboxy-3-methoxy-5-methylthiophene

A solution of LDA was prepared at −10° C. by the addition of 101 mL (0.26 mole) of 2.5 M n-butyllithium to a solution of 25.6 g (0.26 mole) of diisopropylamine in 150 mL of dry THF. This was then slowly added to a colorless solution of 15 g (63 mmole) of 4-bromo-2-carboxy-3-methoxythiophene in 200 mL of dry THF at −78° C. to give a deep red solution. After 1 hr, this solution was cannulated into a solution of 60 g (0.42 mole) of methyl iodide in 300 mL of dry THF at −35° C. The reaction mixture was partitioned with ether and dilute aqueous HCl. The organic layer was dried over $MgSO_4$, filtered and concentrated to a light brown solid. This solid was recrystallized from a mixture of hexane and $CH_2Cl_2$ to give 11 g of a tan solid. mp 166–167° C. $^1$H NMR (300 MHz, $CDCl_3$): δ 3.9 (s, 3H); 2.3 (s, 3H). Anal. Calc'd for $C_7H_7BrO_3S$: C, 33.48; H, 2.81; S, 12.77. Found: C, 33.47; H, 2.77; S, 12.59.

6. Preparation of Methyl 3-Methoxy-5-trifluoromethyl-2-thiophenecarboxylate

To a solution of 20 g (88 mmole) of methyl 3-hydroxy-5-trifluoromethyl-2-thiophenecarboxylate in 200 mL of DMSO was added 37 g (260 mmole) of methyl iodide and 25 g (181 mmole) of powdered $K_2CO_3$. After 2 hr of stirring, the reaction mixture was poured into water and extracted with ether. The organic phase was separated, washed with water several times, dried over $MgSO_4$, filtered and concentrated to give 20 g of a nearly colorless solid. This solid was further purified by recrystallization from 12:1 hexane-:ethyl acetate to give 10.5 g of colorless crystals. The mother liquor was concentrated and purified by column chromatography to give another 8 g (87% yield). mp 78–79° C. $^1$H NMR (300 MHz, $CDCl_3$): δ 7.2 (s, 1H); 4.0 (s, 3H); 3.9 (s, 3H). Anal. Calc'd for $C_8H_7F_3O_3S$: C, 40.00; H, 2.94; S, 13.35. Found: C, 39.87; H, 2.94; S, 13.47.

7. Preparation of 3-Methoxy-5-trifluoromethyl-2-thiophenecarboxylic Acid

A solution of 2 g (14 mmole) of methyl-3-methoxy-5-trifluoromethyl-2-thiophenecarboxylate, 2 g (28 mmole) of KOH in a mixture of 15 mL water and 50 mL of methanol was refluxed for 2 hr. The reaction mixture was partitioned with ether and dilute aqueous HCl. The organic phase was separated, dried over $MgSO_4$, filtered and concentrated to give 2.8 g (87%) of a colorless solid. mp 131–132° C. $^1$H NMR (300 MHz, $CDCl_3$): δ 7.2 (s, 1H); 4.1 (s, 3H). Anal. Calc'd for $C_7H_5F_3O_3S$: C, 37.17; H, 2.23; S, 14.18. Found: C, 36.96; H, 2.19; S, 14.08.

8. Preparation of 4-Benzylthio-3-methoxy-5-trifluoromethyl-2-thiophenecarboxylic Acid To a solution of 3 g (13 mmole) of 3-methoxy-5-trifluoromethyl-2-thiophenecarboxylic acid in 100 mL of dry THF at −20° C. was added 5.3 ml (13 mmole) of 2.5 M n-butyllithium to form a slurry. To this slurry was added a solution of LDA, freshly prepared by the addition of 2.0 g (19.7 mmole) of diisopropylamine and 7.9 mL of 2.5 M n-butyllithium in 50 mL of dry THF. Over 2 hr at 0–5° C., the slurry gradually formed a dark solution, before a solution of 9.8 g (40 mmole) of dibenzyldisulfide was added as a solution in THF. The reaction was stirred and allowed to warm to 15° C. before it was partitioned with ether and dilute aqueous $Na_2CO_3$. The aqueous phase was separated, acidified with 10% aqueous HCl and extracted with fresh ether. The organic phase was separated, concentrated and then purified by reverse phase HPLC using a 50:50 mixture of acetonitrile and water with 0.5% $H_3PO_4$. After most of the acetonitrile was removed in vacuo, the product was recovered from the appropriate fraction by extraction with ether. The organic phase was separated, dried over $MgSO_4$, filtered and concentrated to give 2 g (43%) of a tan solid. mp 146–147° C. $^1$H NMR (300 MHz, $CDCl_3$): δ 9.6 (br, 1H); 7.2 (m, 5H); 4.12 (s, 3H); 4.09 (s, 2H). Anal. Calc'd for $C_{14}H_{11}F_3O_3S_2$: C, 48.27; H, 3.18; S, 18.41. Found: C, 48.00; H, 3.14; S, 18.44.

9. Preparation of 3-Benzylthio-4-methoxy-2-trifluoromethylthiophene

A mixture of 3.6 g of 4-benzylthio-3-methoxy-5-trifluoromethyl-2-thiophenecarboxylic acid and 0.85 g of copper powder in 50 mL of quinoline was heated to 150° C. for 15 min. The mixture was cooled and partitioned with ether and aqueous HCl. The organic phase was separated, dried over $MgSO_4$, filtered, concentrated and purified by column chromatography to give 2.2 g (71%) of an amber oil. $^1$H NMR (300 MHz, $CDCl_3$): δ 7.2 (m, 5H); 6.4 (s, 1H); 4.1 (s, 2H); 3.8 (s, 3H). Anal. Calc'd for $C_{13}H_{11}F_3OS_2$: C, 51.30; H, 3.64; S, 21.07. Found: C, 51.13; H, 3.54; S, 21.02.

10. Preparation of 3-Bromo-4-methoxythiophene

A sample of 15 g of 4-bromo-3-methoxythiophene-2-carboxylic acid was heated to 200–220° C. at 140 mm vacuum for 40 min. A nearly colorless oil (11 g) was collected by distillation. bp. 160–165° C. @ 80–85 mm. This oil was further purified by chromatography to give 8.8 g of a colorless oil. $^1$H NMR (300 MHz, $CDCl_3$): δ 7.2 (d, 1H, J=3.5); 6.2 (d, 1H, J=3.5); 3.9 (s, 3H). Anal. Calc'd for $C_5H_5BrOS$: C, 31.11; H. 2.61; S, 16.61. Found: C, 30.98; H, 2.61; S, 16.89.

The following decarboxylated thiophene compounds were prepared similarly:
3-Bromo-4-ethoxythiophene
  bp 140–145° C. @ 35 mm. $^1$H NMR (300 MHz, $CDCl_3$): δ 7.2 (d, 1H, J=3.5); 6.2 (d, 1H, J=3.5); 4.1 (q, 2H, J=7); 1.5 (t, 3H, J=7). Anal. Calc'd for $C_6H_7BrOS$: C, 34.80; H, 3.41; S, 15.48. Found: C, 34.56; H, 3.36; S, 15.44.
3-Bromo-2-chloro-4-methoxythiophene
  bp 160–165° C. @ 10 mm. mp 63–64° C. $^1$H NMR (300 MHz, $CDCl_3$): δ 6.1 (s, 1H); 3.8 (s, 3H). Anal. Calc'd for $C_5H_4BrClOS$: C, 26.40; H, 1.77; S, 14.09. Found: C, 26.63; H, 1.76; S, 13.95.
3-Bromo-4-methoxy-2-methylthiophene
  bp 150–155° C. @ 10 mm. $^1$H NMR (300 MHz, $CDCl_3$): δ 5.9 (s, 1H); 3.7 (s, 3H); 2.3 (s, 3H). Anal. Calc'd for $C_6H_7BrOS$: C, 34.80; H, 3.41; S, 15.48. Found: C, 34.66; H, 3.57; S, 15.60.
2-Chloro-4-methoxythiophene
  bp 120–125° C. @ 15 mm. $^1$H NMR (300 MHz, $CDCl_3$): δ 6.65 (d, 1H, J=2); 6.0 (d, 1H, J=2); 3.8 (s, 3H). Anal. Calc'd for $C_5H_5ClOS$: C, 40.41; H, 3.20; S, 21.57. Found: C, 40.21; H, 3.20; S, 21.43.

11. Preparation of 5-Chloro-2-chlorosulfonyl-3-methoxythiophene

To a solution of 3.8 g (26 mmol) of 2-chloro-4-methoxythiophene in 100 mL of ether at −30° C. under nitrogen was slowly added 11.2 mL of 2.5 M n-butyllithium. This solution was warmed briefly to room temperature then cooled to −60° C. This solution was then transferred into a solution of 4 g (85 mmol) of $SO_2$ in 300 mL of ether at −30° C. to give a thick slurry. This slurry was diluted to facilitate stirring and allowed to warm to room temperature. The solids were collected by filtration and taken directly into 75 mL of water before adding 75 mL of iso-propyl alcohol. To this was added in portions, 3.8 g (29 mmol) of N-chlorosuccinimide. After 30 min the solution was partitioned with ether and dilute aq. NaHSO$_3$. The organic phase was separated, dried over MgSO$_4$, concentrated and purified by HPLC to give 3.1 g of an amber oil. $^1$H NMR (300 MHz, CDCl$_3$): δ 6.8 (s, 1H); 4.1 (s, 3H). Anal. Calc'd for C$_5$H$_4$Cl$_2$O$_3$S$_2$: C, 24.30; H, 1.63; S, 25.95. Found: C, 24.10; H, 1.59; S, 25.65.

The following 2-chlorosulfonylthiophene compound was prepared similarly:
2-Chlorosulfonyl-3-methoxythiophene mp 71–72° C. $^1$H NMR (300 MHz, CDCl$_3$): δ 7.7 (d, 1H, J=5.6); 7.0 (d, 1H, J=5.6); 4.1 (s, 3H). Anal. Calc'd for C$_5$H$_5$ClO$_3$S$_2$: C, 28.24; H, 2.37; S, 30.15. Found: C, 28.41; H, 2.33; S, 30.18.

12. Preparation of 3-chlorosulfonyl-2-methoxythiophene

To a solution of 9 g (47 mmol) of 3-bromo-2-methoxythiophene in 150 mL of dry THF at −78° C. was slowly added 19 mL of 2.5 M n-butyllithium. After 30 min, the solution was sparged with excess anhydrous SO$_2$ to precipitate a colorless solid. This mixture was warmed to room temperature, diluted with ether and the solid collected by filtration. This solid was dissolved in 150 mL of an equal mixture of iso-propyl alcohol and water. To this solution was added in portions, 6.7 g (50 mmol) of N-chlorosuccinimide. After 15 min, the reaction solution was partitioned with ether and dilute aqueous NaHSO$_3$. The organic phase was separated, dried over MgSO$_4$, filtered, concentrated and purified by column chromatography to give 5.1 g of an amber oil. $^1$H NMR (300 MHz, CDCl$_3$): δ 6.2 (S, 1H); 3.9 (s, 3H). Anal. Calc'd for C$_5$H$_5$ClO$_3$S$_2$: C, 28.24; H, 2.37; S, 30.15. Found: C, 28.56; H, 2.57; S, 29.96.

The following 3-chlorosulfonylthiophene compounds were prepared similarly:
3-Chlorosulfonyl-4-methoxythiophene $^1$H NMR (300 MHz, CDCl$_3$): δ 8.1 (d, 1H, J=3.8); 6.4 (d, 1H, J=3.8); 4.0 (s, 3H). Anal. Calc'd for C$_5$H$_5$ClO$_3$S$_2$: C, 28.24; H, 2.37; S, 30.15. Found: C, 28.24; H, 2.37; S, 29.85.
3-Chlorosulfonyl-4-ethoxythiophene $^1$H NMR (300 MHz, CDCl$_3$): δ 8.1 (d, 1H, J=3.5); 6.4 (d, 1H, J=3.5); 4.2 (q, 2H, J=6.9); 1.2 (t, 3H, J=6.9). Anal. Calc'd for C$_6$H$_7$ClO$_3$S$_2$: C, 31.79; H, 3.11; S, 28.28. Found: C, 32.07; H, 3.19; S, 27.97.
2-Chloro-3-chlorosulfonyl-4-methoxythiophene $^1$H NMR (300 MHz, CDCl$_3$): δ 6.2 (s, 1H); 3.9 (s, 3H). Anal. Calc'd for C$_5$H$_5$Cl$_2$O$_3$S$_2$: C, 28.24; H, 2.37; S, 30.15. Found: C, 28.56; H, 2.57; S, 29.96.
3-Chlorosulfonyl-4-methoxy-2-methylthiophene $^1$H NMR (300 MHz, CDCl$_3$): δ 6.0 (s, 1H); 3.8 (s, 3H); 2.6 (s, 3H). Anal. Calc'd for C$_6$H$_7$ClO$_3$S$_2$: C, 28.24; H, 2.37; S, 30.15. Found: C, 28.56; H, 2.57; S, 29.96.

13. Preparation of 3-Chlorosulfonyl-4-methoxy-2-trifluoromethylthiophene

A stirred mixture of 5.3 g (17.4 mmole) of 3-benzylthio-4-methoxy-2-trifluoromethylthiophene in 250 mL of CH$_2$Cl$_2$ and 250 mL of dilute aqueous HCl at 0° C. was sparged slowly with 4.7 g of Cl$_2$. The mixture was warmed to room temperature and the organic phase was separated, dried over MgSO$_4$, filtered and concentrated to an amber oil. This oil was purified by HPLC to give 3 g of a colorless oil. $^1$H NMR (300 MHz, CDCl$_3$): δ 6.6 (s, 1H); 4.0 (s, 3H). Anal. Calc'd for C$_6$H$_4$ClF$_3$O$_3$S$_2$: C, 25.68; H, 1.44; S, 22.85. Found: C, 25.98; H, 1.5; S, 22.65.

14. Preparation of 3-Amino-8-chloro-5-methylthio[1,2,4]triazolo[4,3-c]pyrimidine Hydrobromide A solution of 40 mL (120 mmol) of 3 molar cyanogen bromide in dichloromethane was combined with 19.0 g (100 mmol) of 5-chloro-4-hydrazino-2-methylthiopyrimidine and 200 mL of dry isopropyl alcohol at ambient temperature with stirring. The resulting mixture was stirred for 18 hours and then diluted with 500 mL of diethyl ether. The solids that formed were recovered by filtration and dried to obtain the theoretical amount of the title compound as a yellow solid melting above 250° C. $^1$H NMR (DMSO-d$_6$): δ 7.80 (s, 1H); 2.67(s, 3H); $^{13}$C: δ 150.96, 147.90, 143.10, 138.38, 113.16, 14.22. Anal. Calc'd for C$_6$H$_7$N$_5$BrClS: C, 24.3; H, 2.38; N, 23.6; S, 10.8. Found: C, 26.1; H, 2.69; N, 24.0; S, 12.2.

The following 3-amino[1,2,4]triazolo-[4,3-c]pyrimidine compounds were prepared similarly:
3-Amino-8-methoxy-5-methylthio[1,2,4]triazolo[4,3-c]pyrimidine hydrobromide—a tan solid melting at 180–182° C.; Anal. Calc'd for C$_7$H$_{10}$N$_5$BrOS: C, 28.8; H, 3.45; N, 24.0; S, 11.0. Found: C, 29.0; H, 3.44; N, 23.9; S, 11.1.
3-Amino-8-methyl-5-methylthio[1,2,4]triazolo[4,3-c]pyrimidine Hydrobromide—a yellow solid melting at 234–236° C.; Anal. Calc'd for C$_7$H$_{10}$N$_5$BrS: C, 30.6; H, 3.30; N, 25.5; S, 11.7. Found: C, 30.7; H, 3.52; N, 25.3; S, 11.5.

15. Preparation of 2-Amino-8-chloro-5-methoxy[1,2,4]triazolo[1,5-c]pyrimidine A mixture of 15.0 g (51 mmol) of 3-amino-8-chloro-5-methylthio[1,2,4]triazolo[4,3-c]pyrimidine hydrobromide, 8.2 mL (76 mmol) of ethyl acrylate, and 150 mL of methanol was prepared and cooled in an ice bath. A solution of 17 mL (76 mmol) of 4.5 molar sodium methoxide in methanol was added to this slowly with cooling and stirring. When the addition was complete, the mixture was allowed to warm to ambient temperature and was stirred for 18 hours. It was then neutralized with 2.0 mL of acetic acid. The solids that formed were recovered by filtration, washed with diethyl ether, and dried to obtain 7.7 g (75 percent of theory) of the title compound as a tan powder melting above 250° C. $^1$H NMR (DMSO-d$_6$): δ 8.0(s, 1H); 6.6 (brs, 2H); 4.1 (s, 3H); $^{13}$C: δ 166.40, 151.65, 147.73, 140.95, 108.57, 56.12. Anal. Calc'd for C$_6$H$_6$N$_5$ClO: C, 36.1; H, 3.03; N, 35.1. Found: C, 36.1; H, 3.19; N, 34.8.

The following 2-amino[1,2,4]triazolo[1,5-c]pyrimidine compounds were prepared similarly:
2-Amino-5,8-dimethoxy[1,2,4]triazolo[1,5-c]pyrimidine—a tan powder melting at 201–203° C.; Anal. Calc'd for C$_7$H$_9$N$_5$O$_2$: C, 43.1; H, 4.65; N, 35.9. Found: C, 43.2; H, 4.67; N, 35.6.
2-Amino-8-methyl-5-methoxy[1,2,4]triazolo[1,5-c]pyrimidine—a tan solid melting above 250° C.; Anal. Calc'd for C$_7$H$_9$N$_5$O: C, 46.9; H, 5.06; N, 39.1. Found: C, 46.7; H, 4.84; N, 39.1.

16. Preparation of 2-Amino-5,8-dimethoxy[1,2,4]triazolo[1,5-a]pyridine

A mixture of 58.4 g (0.21 mole) of ethyl [(3,6-dimethoxypyridin-2-yl)amino]carbonothioylcarbamate, 70 g (1 mole) of hydroxylamine hydrochloride and 105 mL (0.6 mole) of diisopropylethylamine in 1 liter of ethanol was heated to reflux for 12 hr. After cooling, the resulting solution was evaporated to dryness under vacuum. Water (250 ml) and diethyl ether (100 ml) were added to the residue and the mixture was stirred for 15 min. The product was collected by filtration and dried under a vacuum at room temperature to give 25.2 g of 2-amino-5,8-dimethoxy[1,2,4]triazolo[1,5-a]pyridine.

mp 223–234° C. $^1$H NMR (DMSO-d$_6$): δ 6.9 (d, 1H, j=8.7); 6.2 (d, 1H, j=8.4); 5.9 (s, 2H); 4.0 (s, 3H); 3.8 (s, 3H).

17. Preparation of 2-Amino-5,7-dimethoxy[1,2,4]triazolo[1,5-a]pyrimidine

2-Amino-4,6-dimethoxypyrimidine (5.0 g, 36 mmol) was dissolved in dry tetrahydrofuran (THF, 35 mL), ethoxycarbonylisothiocyanate (6.4 mL, 54 mmol) was added and the solution was allowed to stir at room temperature. After 24 hours, the solvent is removed in vacuo and the residue was mixed with ether to form a crystalline solid. The solids were removed by vacuum filtration and dried to afford ethyl [(4,6-dimethoxypyrimidin-2-yl)amino]carbono thioylcarbamate as a tan solid (8.9 g, 87%). mp 196–197° C. $^1$H NMR (CDCl$_3$): δ 13.2 (bs, 1H); 8.8 (bs, 1H); 5.80 (s, 1H); 4.32–4.25 (q, 2H, J=7.2); 3.93 (s, 3H); 1.30 (t, 3H, J=7.2).

Ethyl [(4,6-dimethoxypyrimidin-2-yl)amino carbonothioylcarbamate (0.50 g, 1.7 mmol) was mixed with ethanol (5 mL). To this mixture was added hydroxylamine hydrochloride (0.12 g, 1.7 mmol) and diisopropylethyl-amine (0.30 mL, 1.7 mmol). The resulting mixture was allowed to stir at room temperature. After 2.5 hours, additional diisopropylethylamine (0.30 mL, 1.7 mmol) was added to the mixture. After 48 hours the ethanol was removed in vacuo and the residue was partitioned between H$_2$O and Et$_2$O to give a powder. The powder was filtered and dried to afford the product as a tan powder (0.27 g, 82%). mp 215–220° C. Anal: Cacld for C$_7$H$_9$N$_5$O$_2$: C, 43.08; H, 4.65; N, 35.88; O, 16.39; found: C, 39.88; H, 4.22; N, 32.00; O, 16.35. $^1$H NMR (DMSO-d$_6$): δ 6.04 (s, 1H); 5.97 (br, 2H); 4.04 (s, 3H).

18. Preparation of 3-Methoxy-N-(5,8-dimethoxy[1,2,4]triazolo[1,5-c]pyrimidin-2-yl)thiophene-2-sulfonamide (Compound 1)

To a slurry of 0.8 g (4.5 mmol) of 2-amino-5,8-dimethoxy [1,2,4]triazolo[1,5-c]pyrimidine in 7 mL of acetonitrile was added 1.3 g (6.1 mmol) of 3-methoxythiophene-2-sulfonylchloride, 0.6 mL of dry pyridine and 0.003 mL of dry DMSO. After 96 hr, the reaction mixture was partitioned with CH$_2$Cl$_2$ and water. The organic phase was separated, washed with dilute aqueous HCl, dried over MgSO$_4$, filtered and concentrated. The residue was taken into a small amount of CH$_2$Cl$_2$ before ether was added slowly with stirring to precipitate a fine tan solid. The solid was collected by filtration and dried under vacuum to give 0.85 g (50%) of the desired product. mp 227–228° C. $^1$H NMR (300 MHz, DMSO-d$_6$): δ 12.1 (s, 1H); 7.8 (d, 1H, J=5.6); 7.6 (s, 1H); 7.0 (d, 1H, J=5.6); 4.1 (s, 3H); 3.9 (s, 3H); 3.8 (s, 3H). Calc'd for C$_{12}$H$_{13}$N$_5$O$_5$S$_2$: C, 38.81; H, 3.53; N, 18.86; S, 17.27. Found: C, 38.32; H, 3.49; N, 18.91; S, 17.34.

The N-([1,2,4]triazolo[1,5-c]pyrimidin-2-yl)thiophenesulfonamide, N-([1,2,4]triazolo[1,5-a]pyrimidin-2-yl)thiophenesulfonamide, and N-([1,2,4]triazolo[1,5-a]pyridin-2-yl)thiophenesulfonamide compounds of Tables 1 and 2 were prepared similarly.

19. Preparation of Herbicidal Compositions

Wettable Powder

Barden clay (55.5 g), HiSil 233 silica (5.0 g), Polyfon H (sodium lignosulfonate; 7.0 g), Stepanol ME-Dry (sodium lauryl sulfate; 7.9 g), and Compound 1 (20.4 g) were added to a 1 quart glass Waring blender cup and thoroughly mixed at high speed. The combined mixture was passed (one time) thru a laboratory Trost mill with the opposing jets set between 75 and 80 psi (517–551 kPa). This produced a wettable powder of excellent wettability and suspension power. By diluting this wettable powder with water it is possible to obtain suspensions of suitable concentrations for controlling weeds.

Aqueous Suspension Concentrate

To prepare an aqueous suspension concentrate, deionized water (106 g), Kelzan S (xanthan gum; 0.3 g), Avicel CL-611 (carboxylmethyl cellulose; 0.4 g), and Proxel GXL (1,2-benzisothiazolin-3-one; 0.2 g) were added to a blender and mixed for 30 min. Then Compound 6 (44 g), Darvan #1 (naphthalene sulfonate; 2 g), Foamaster UDB (silicone fluid; 0.2 g), Pluronic P-105 (ethylene oxide/propylene oxide block copolymer; 20 g), phosphoric acid (0.02 g), and propylene glycol (16 g) were added to the same blender and mixed for 5 min. Once blended the contents were milled in an Eiger mill filled with 1–1.25 mm lead free glass beads (40 mL) at 5000 rpm for 30 min. External cooling on the Eiger mill grinding chamber was maintained at 15° C.

Oil-based Suspension Concentrate

To a 1 quart glass Waring blender cup was added Exxon's crop oil (145.4 g), Amsul DMAP 60 (dimethylaminopropane salt of dodecybenzene sulfonic acid; 4.0 g) and Attagel 50 (attapulsite clay; 4.0 g). The mixture was thoroughly blended at high speed to insure homogeneity. The Amsul DMAP was difficult to disperse, but eventually formed small homogeneous globules. Agrimul 70-A (ethoxylated bismethylene octylphenol; 4.0 g) and Emulsogen M (oleyl alcohol-ethylene oxide; 16.0 g) were added and thoroughly blended until the mixture was uniform in texture. Cloquintocet mexyl (5.4 g) was then blended into the mixture followed by Compound 7 (21.3 g). The final grinding stock dispersion milled in the Eiger mill using the conditions described above for the aqueous suspension concentrate.

20. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The plants were employed for testing when they reached the first or second true leaf stage.

A weighed amount of each test compound, determined by the highest rate to be tested, was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, iso-propyl alcohol, dimethyl sulfoxide, Atplus 411F crop oil concentrate, and Triton X-155 surfactant (methylenebisdiamyl phenoxy polyethoxy ethanol) in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 3.

dissolve readily, the mixture was warmed and/or sonicated. The stock solutions obtained were diluted with a 99.9:0.1 mixture of water and Tween® 155 surfactant (ethoxylated sorbitan fatty acid ester) to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous

TABLE 3

POSTMERGENCE HERBICIDAL ACTIVITY

| Cpd. No. | Rate, ppm | STEME | XANST | CHEAL | IPOHE | AMARE | ABUTH | VIOTR | POLCO | ALOMY | SETFA | SORBI | AVEFA |
|---|---|---|---|---|---|---|---|---|---|---|---|---|---|
| 1 | 3.9 | 75 | 50 | 75 | 85 | 95 | 75 | 70 | 98 | 95 | 100 | 98 | 99 |
| 2 | 7.8 | 98 | 60 | 90 | 85 | 98 | 95 | 95 | 90 | 70 | 98 | 98 | 90 |
| 3 | 31 | 70 | 100 | 95 | 70 | 100 | 70 | 80 | 85 | 70 | 85 | 90 | 80 |
| 4 | 15.6 | 60 | 60 | 90 | 60 | 100 | 70 | 60 | 90 | 70 | 85 | 70 | 60 |
| 6 | 7.8 | 80 | 95 | 80 | 85 | 100 | 90 | 85 | 85 | 80 | 98 | 80 | 70 |
| 7 | 1.9 | 98 | 80 | 60 | 80 | — | 80 | 80 | — | 98 | 100 | 98 | 98 |
| 8 | 7.8 | 95 | 60 | 70 | 60 | — | 75 | 75 | — | 50 | 60 | 95 | 85 |
| 9 | 62 | 95 | 60 | 40 | 70 | — | 70 | 60 | — | 60 | 20 | 70 | 10 |
| 10 | 15.6 | 98 | 100 | 70 | 80 | 95 | 90 | 90 | 70 | 50 | 90 | 80 | 80 |
| 11 | 15.6 | 80 | 90 | 95 | 70 | 100 | 85 | 75 | 80 | 75 | 100 | 90 | 85 |
| 12 | 15.6 | 95 | 90 | 90 | 95 | 95 | 95 | 80 | 85 | 60 | 95 | 95 | 85 |
| 13 | 7.8 | 95 | 95 | 90 | 75 | 100 | 95 | 75 | 990 | 80 | 95 | 95 | 85 |
| 14 | 31.3 | 100 | 95 | 100 | 80 | 95 | 90 | 75 | 95 | 80 | 95 | 95 | 80 |
| 15 | 15.6 | 90 | 90 | 90 | 70 | 90 | 70 | 70 | 80 | 80 | 100 | 100 | 95 |
| 16 | 15.6 | 90 | 95 | 95 | 60 | 95 | 80 | 70 | 90 | 85 | 90 | 90 | 80 |
| 17 | 31.3 | 90 | 95 | 100 | 70 | 95 | 85 | 70 | 60 | 70 | 90 | 90 | 85 |
| 18 | 15.6 | 90 | 100 | 90 | 75 | 100 | 85 | 100 | 95 | 70 | 90 | 100 | 95 |
| 19 | 15.6 | 95 | 95 | 100 | 80 | 100 | 80 | 100 | 95 | 70 | 100 | 100 | 100 |
| 20 | 31.3 | 85 | 100 | 75 | 75 | 95 | 85 | 90 | 90 | 30 | 50 | 85 | 70 |
| 21 | 62.5 | 100 | 90 | 100 | 80 | 100 | 100 | 90 | 100 | 30 | 50 | 100 | 75 |
| 22 | 31.3 | 80 | 90 | 90 | 90 | 100 | 70 | 80 | 90 | 60 | 80 | 95 | 50 |
| 23 | 15.6 | 80 | 90 | 80 | 40 | 90 | 90 | 70 | 75 | 70 | 90 | 90 | 70 |
| 24 | 7.8 | 80 | 90 | 85 | 80 | 100 | 70 | 70 | 70 | 80 | 90 | 100 | 70 |
| 25 | 31 | 60 | 90 | 90 | 70 | 90 | 70 | 70 | 70 | 80 | 80 | 95 | 80 |

STEME = chickweed (*Stellaria media*)
XANST = cocklebur (*Xanthium strumarium*)
CHEAL = lambsquarters (*Chenopodium album*)
IPOHE = morningglory (*Ipomoea hederacea*)
AMARE = pigweed (*Amaranthus retroflexus*)
ABUTH = velvetleaf (*Abutilion theophrasti*)
VIOTR = viola (*Viola tricolor*)
POLCO = wild buckwheat (*Polygonum convolvulus*)
ALOMY = blackgrass (*Alopecurus myosuroides*)
SETFA = giant foxtail (*Setaria faberi*)
SORBI = Rox orange sorghum (*Sorghum bicolor*)
AVEFA = wild oats (*Avena fatua*)

21. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not mixture. A highest application rate of 4.48 kg/ha is achieved when 50 mg of test compound is employed.

The treated pots and control pots were placed in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 4.

TABLE 4

PREEMERGENCE HERBICIDAL ACTIVITY

| Cpd. No. | Rate, g/Ha | XANST | CHEAL | IPOHE | AMARE | ABUTH | EPHHL | ALOMY | ECHCG | DIGSA | SETFA | SORBI | AVEFA |
|---|---|---|---|---|---|---|---|---|---|---|---|---|---|
| 1 | 17.5 | 70 | 98 | 85 | 100 | 98 | 100 | 100 | 100 | 100 | 100 | 100 | 100 |
| 2 | 8.8 | — | 98 | 80 | 95 | 75 | 90 | 95 | 75 | 100 | 100 | 100 | 100 |
| 3 | 35 | 70 | 95 | 60 | 95 | 50 | 70 | 80 | 70 | 95 | 90 | 90 | 70 |
| 4 | 35 | 0 | 80 | 50 | 100 | 70 | 40 | 95 | 0 | 90 | 90 | 80 | 60 |
| 6 | 35 | 70 | 99 | 80 | 100 | 80 | 70 | 75 | 80 | 100 | 100 | 100 | 80 |
| 7 | 4.4 | 80 | — | 85 | 95 | 95 | 85 | 100 | 99 | 100 | 100 | 100 | 100 |
| 8 | 8.8 | 80 | 70 | 75 | 80 | 70 | 85 | 85 | 25 | 50 | 60 | 70 | 80 |
| 9 | 70 | 25 | — | 10 | 40 | 30 | 10 | 100 | 0 | 10 | 15 | 50 | 30 |
| 10 | 8.8 | — | 95 | 80 | 100 | 70 | 75 | 90 | 90 | 70 | 90 | 100 | 90 |
| 11 | 4.4 | 50 | 95 | 30 | 90 | 80 | 50 | 100 | 10 | 40 | 100 | 98 | 70 |
| 12 | 8.8 | 90 | 100 | 80 | 100 | 90 | 95 | 100 | 100 | 100 | 100 | 100 | 100 |
| 13 | 4.4 | 80 | 100 | 90 | 90 | 80 | 100 | 100 | 100 | 100 | 100 | 100 | 100 |
| 14 | 35 | 60 | 98 | 60 | 80 | 80 | 30 | 100 | 98 | 100 | 100 | 100 | 100 |
| 15 | 8.8 | 60 | 98 | 70 | 85 | 90 | 90 | 100 | 80 | 100 | 100 | 100 | 100 |
| 16 | 35 | 40 | 80 | 0 | 60 | 40 | 0 | 100 | 0 | 30 | 0 | 0 | 0 |
| 17 | 35 | 70 | 100 | 0 | 70 | 30 | 60 | 100 | 30 | 30 | 60 | 60 | 30 |
| 18 | 4.4 | 90 | 100 | 80 | 95 | 90 | 90 | 100 | 100 | 98 | 100 | 100 | 80 |
| 19 | 8.8 | 50 | 90 | 90 | 75 | 95 | 90 | 95 | 95 | 100 | 100 | 95 | 100 |
| 20 | 17.5 | 60 | 70 | 70 | 80 | 80 | 50 | 90 | 95 | 85 | 50 | 90 | 90 |
| 21 | 8.8 | 50 | 70 | 40 | 60 | 80 | 60 | 70 | 30 | 40 | 70 | 70 | 70 |
| 22 | 35 | 80 | 98 | 98 | 100 | 100 | 80 | 70 | 100 | 98 | 100 | 100 | 70 |
| 23 | 4.4 | 70 | 90 | 80 | 100 | 90 | 90 | 98 | 80 | 100 | 98 | 100 | 90 |
| 24 | 8.8 | 70 | 100 | 98 | 90 | 98 | 80 | 90 | 40 | 98 | 100 | 100 | 70 |
| 25 | 17.5 | 50 | 90 | 60 | 95 | 80 | 80 | 95 | 85 | 85 | 85 | 90 | 80 |

XANST = cocklebur (*Xanthium strumarium*)
CHEAL = lambsquarters (*Chenopodium album*)
IPOHE = morningglory (*Ipomoea hederacea*)
AMARE = pigweed (*Amaranthus retroflexus*)
ABUTH = velvetleaf (*Abutilion theophrasti*)
EPHHL = wild poinsettia (*Euphorbia heterophylla*)
ALOMY = blackgrass (*Alopecurus myosuroides*)
ECHCG = barnyardgrass (*Echinochloa crus-galli*)
DIGSA = crabgrass (*Digitaria sanguinalis*)
SETFA = giant foxtail (*Setaria faberi*)
SORBI = Rox orange sorghum (*Sorghum bicolor*)
AVEFA = wild oats (*Avena fatua*)

What is claimed is:

1. An N-(triazoloazinyl)thiophenesulfonamide compound of the formula (I):

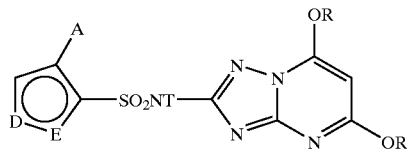

(I)

wherein
  D and E represent S or CB with the proviso that one of D or E is S;
  A and B independently represent H, halo, $CF_3$, R, OR' or $CO_2R''$;
  T represents H, $SO_2R''$, $C(O)R''$, $C(O)OR''$, $C(O)NR''_2$, or $CH_2CH_2C(O)OR''$;
  R represents $CH_3$ or $CH_2CH_3$;
  R' represents $C_1$–$C_4$ alkyl, $C_3$–$C_4$ alkenyl, or $C_3$–$C_4$ alkynyl each optionally possessing up to two chloro, bromo or $O(C_1$–$C_4)$alkyl substituents or up to the maximum possible number of fluoro substituents;
  R'' represents H or $C_1$–$C_4$ alkyl;
and, when T represents H, the agriculturally acceptable salts thereof.

2. A compound of claim 1 in which T represents H or an agriculturally acceptable salt thereof.

3. A compound of claim 1 in which D represents S and E represents CB.

4. A compound of claim 3 in which B represents $CO_2R''$.

5. A compound of claim 1 in which A represents OR' or $CO_2R''$.

6. A composition comprising an herbicidal amount of an N-(triazoloazinyl)thiophenesulfonamide compound of the formula (I):

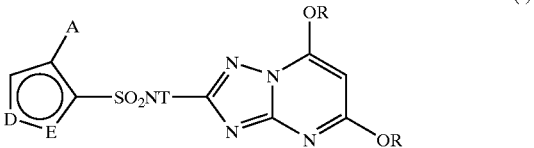

(I)

wherein
  D and E represent S or CB with the proviso that one of D or E is S;
  A and B independently represent H, halo, $CF_3$, R, OR' or $CO_2R''$;
  T represents H, $SO_2R''$, $C(O)R''$, $C(O)OR''$, $C(O)NR''_2$, or $CH_2CH_2C(O)OR''$;
  R represents $CH_3$ or $CH_2CH_3$;
  R' represents $C_1$–$C_4$ alkyl, $C_3$–$C_4$ alkenyl, or $C_3$–$C_4$ alkynyl each optionally possessing up to two chloro, bromo or $O(C_1$–$C_4)$alkyl substituents or up to the maximum possible number of fluoro substituents;

R" represents H or $C_1$–$C_4$ alkyl;

and, when T represents H, the agriculturally acceptable salts thereof, in admixture with an agriculturally acceptable adjuvant or carrier.

7. A composition of claim 6 in which T represents H or an agriculturally acceptable salt thereof.

8. A composition of claim 6 in which D represents S and E represents CB.

9. A composition of claim 8 in which B represents $CO_2R"$.

10. A composition of claim 6 in which A represents OR' or $CO_2R"$.

11. A method of controlling undesirable vegetation which comprises applying to the vegetation or to the locus thereof an herbicidally effective amount of an N-(triazoloazinyl) thiophenesulfonamide compound of the formula (I):

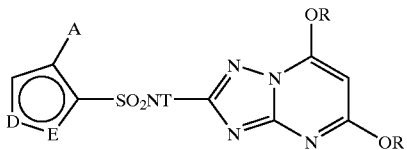

wherein
D and E represent S or CB with the proviso that one of D or E is S;

A and B independently represent H, halo, $CF_3$, R, OR' or $CO_2R"$;

T represents H, $SO_2R"$, C(O)R", C(O)OR", C(O)NR"$_2$, or $CH_2CH_2C(O)OR"$;

R represents $CH_3$ or $CH_2CH_3$;

R' represents $C_1$–$C_4$ alkyl, $C_3$–$C_4$ alkenyl, or $C_3$–$C_4$ alkynyl each optionally possessing up to two chloro, bromo or $O(C_1$–$C_4)$alkyl substituents or up to the maximum possible number of fluoro substituents;

R" represents H or $C_1$–$C_4$ alkyl;

and, when T represents H, the agriculturally acceptable salts thereof.

12. A method of claim 11 in which T represents H or an agriculturally acceptable salt thereof.

13. A method of claim 11 in which D represents S and E represents CB.

14. A method of claim 13 in which B represents $CO_2R"$.

15. A method of claim 11 in which A represents OR' or $CO_2R"$.

\* \* \* \* \*